Figure 1:
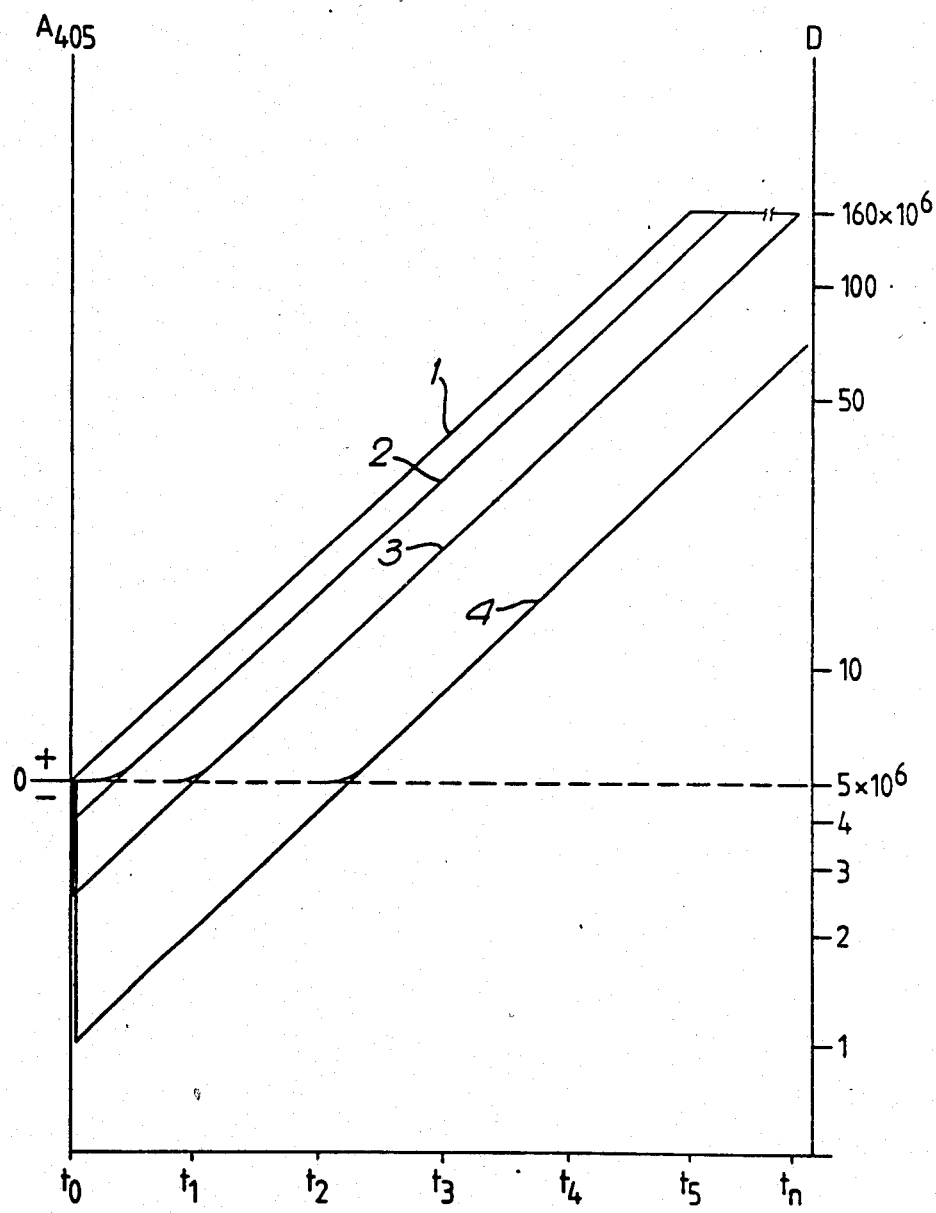

United States Patent [19]

Falck

[11] Patent Number: 4,675,288

[45] Date of Patent: Jun. 23, 1987

[54] METHOD FOR THE PERFORMANCE OF A MUTAGENICITY TEST

[75] Inventor: Kai Falck, Helsinki, Finland

[73] Assignee: Labsystems Oy, Helsinki, Finland

[21] Appl. No.: 585,375

[22] PCT Filed: Jul. 11, 1983

[86] PCT No.: PCT/FI83/00053

§ 371 Date: Feb. 27, 1984

§ 102(e) Date: Feb. 27, 1984

[87] PCT Pub. No.: WO84/00384

PCT Pub. Date: Feb. 2, 1984

[30] Foreign Application Priority Data

Jul. 12, 1982 [FI] Finland ............................ 82/2473

[51] Int. Cl.$^4$ .................. C12Q 1/04; C12Q 1/02; C12Q 1/68

[52] U.S. Cl. ........................... 435/34; 435/29; 435/6

[58] Field of Search .................. 435/6, 29, 172.1, 34

[56] References Cited

U.S. PATENT DOCUMENTS

| | | | |
|---|---|---|---|
| 3,255,095 | 6/1966 | Ricard | 435/34 |
| 4,072,574 | 2/1978 | Loeb et al. | 435/6 |
| 4,256,832 | 3/1981 | Findl et al. | 435/6 |
| 4,299,915 | 11/1981 | Thilly et al. | 435/6 |
| 4,345,026 | 8/1982 | Lew | 435/6 X |

FOREIGN PATENT DOCUMENTS 1358760 7/1974 United Kingdom .

OTHER PUBLICATIONS

Husimi et al., Rev. Sci. Instrum., 53(4), pp. 517–522, Apr. 1982

Coultas et al., J. of Bacteriology, vol. 84, pp. 393–401, 1962.

*Primary Examiner*—Sidney Marantz
*Assistant Examiner*—Shawn P. Foley
*Attorney, Agent, or Firm*—Hopgood, Calimafde

[57] ABSTRACT

Method for the performance of a mutagenicity test so that a cell population is subjected to a mutagen. As a result of this, a part of the population mutates, whereat the originally uniform cell population is differentiated into sub-populations. The variation of turbidity caused by the increase in the density of the differentiated cell populations is measured as a change in optical density by means of a photometer measuring vertically at a certain wavelength, and the quantity of cells in the sub-populations is determined as optical density. The absorbance values are measured in accordance with a pre-programmed time share system and a growth curve is formed out of the values as a function of time.

3 Claims, 3 Drawing Figures

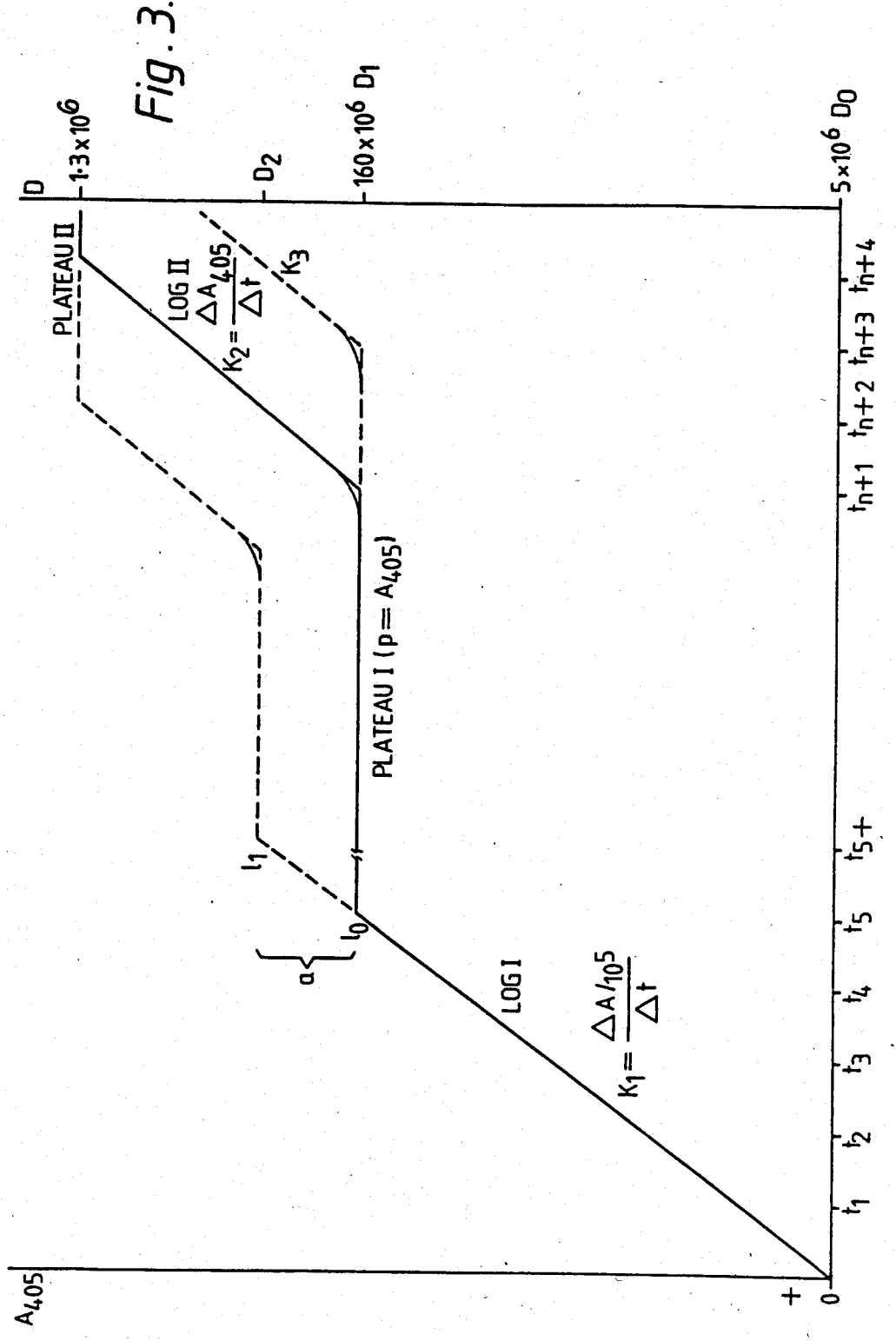

METHOD FOR THE PERFORMANCE OF A MUTAGENICITY TEST

The present invention is concerned with a method for the performance of a mutagenicity test so that a cell population is subjected to a mutagen, as a result of which a part of the population mutates, whereat the originally uniform cell population is differentiated into sub-populations.

Mutagenicity testing is used for rapid preliminary testing of substances suspected as carcinogens, for in bacterial mutagenicity tests it has been established that at least 90% of known carcinogens are also mutagens. Out of biological samples, it is possible to establish, e.g. in the form of mutagenic activity of urine, that a person concerned has perhaps been exposed to mutagenic substances, which, thus, potentially cause the risk of cancer.

It is possible to determine mutagens present in the samples of air, water and foods and, e.g., possible traces of mutagenic pesticides etc. agents in foods.

Mutagenicity testing is to an ever increasing extent a part of the statutory toxicological analysis of a product or equivalent. Some of the most important users of these tests are at present the pharmaceutical and chemical industries. A specific field of their own is formed by the authorities dealing with environmental protection and with occupational safety, who must usually examine complex samples containing several different chemicals. Along with the increasing legislation for the protection of consumers, e.g., foods and food additives are also being included in the scope of mutagenicity studies. The testing of these samples may become problematic, because of the growth factors contained in the said products may cause false positive results.

In prior art, a microbiological fluctuation test has been used for the testing of mutagenicity. The fluctuation test is a two-stage test of bacterial mutagenicity, which is suitable for the testing of low, non-toxic concentrations of mutagenic substances. In the first test stage, which takes 18 to 20 hours, the mutation, if any, takes place. After that a selection of 3 days takes place in a growth medium free from growth-factors.

Since the test takes place in a liquid medium in which attempts are made to isolate each original mutant, it follows from the above requirement that the performance of the test requires a great number of test tubes. The more test tubes are available per sample, the higher is the probability that the original mutants produced can be isolated each of them in its own tube.

The observation of mutant growth is based on the use of a pH-indicator, for the mutated cells excrete acid fermentation products when growing in the selection medium.

The microbiological fluctuation test is one of the most sensitive mutagenicity tests that have been developed by now. The Ames test, which is the most common bacterial mutagenicity test in use, requires about 10 to 100 times higher concentrations of mutagens to give a similar positive response as compared with the fluctuation test.

A drawback of the fluctuation test is its sensitivity to the toxic and growth-factor effects of the substance, and that is why the test requires lots of work. Per one sample, at least 50 test tubes are used and, if the sample is unknown in respect of its toxic properties, up to eight different dilutions of the said sample may be required in order to reach non-toxic, but still mutagenic concentration ranges. In such a case, the total number of tubes may be up to 400 per sample. Including all the working steps, the performance of the test takes about 30 min. per dilution (50 tubes), which restricts the number of samples to be analyzed considerably. The mutagenization and selection to be performed on subsequent days restrict the starting days of the test to Mondays and Thursdays only, if working during the weekends is to be avoided. A drawback of the mutageneity test performed manually is the high cost.

The method in accordance with the present invention is mainly characterized in that the variation of turbidity caused by the change in the density of the differentiated cell populations is measured as a change in optical density by means of a photometer measuring vertically at a certain wavelength and the quantity of cells in the sub-populations is determined as optical density.

By means of a photometer measuring vertically, it is possible to measure the quantity of cells in a population of bacteria precisely as optical density, whereat the measurement result is not affected by sedimentation of the cells or by variations in the liquid volume. Besides by means of a photometer, the measurement may also be performed by means of a vertically measuring fluorometer, nephelometer, luminometer, or any other apparatus that is capable of registering variation in the growth of cell populations.

An originally uniform auxotrophic cell population may be differentiated genetically by the effect of a mutagen into auxotrophic and prototrophic sub-populations. By, by means of a photometer, observing the growth of the said populations, which may take place in one common cuvette, it is possible to find out, from the growth curve produced as a function of time, e.g., the mutageneity of the sample, toxicity, nature of toxicity (bacteriostat, bactericide), decomposition of a toxic compound during the test, as well as growth factors, if any, present in the sample, and growth rates of the auxotrophic and prototrophic cells. In order to find out these parameters, it is not necessary to interfere with the sample itself or with the test organisms.

In order to establish the spontaneous mutation frequency (so-called background), a sample corresponding to the other samples but not containing mutagens is required. The operability of the method is confirmed by a corresponding sample that contains known mutagens. Depending on the unknown sample to be studied, it is possible to make several parallel assays and/or dilutions of it.

In a microbiological mutagenicity test, it is possible to use genetically precisely characterized amino-acid auxotrophic single-marker bacterial strains. A change in the genotype caused by mutation is detected as phenotypically changed growth-factor requirements so that the cells that have obtained a correct type of mutation have become independent from the effect of the growth-factor amino acids.

In the test, the originally genetically uniform population of bacteria is subjected to mutagens, as a result of which a part of the population mutates from auxotrophic to prototrophic. The increase in the turbidity of the sub-populations in this way differentiated can be observed spectrophotometrically in the sub-minimal growth medium by means of a FP-901 photometer by vertical measurement, whereat changes in liquid volume and sedimentation of bacterial cells do not affect the measurement result of the absorbance. A photometer of the type FP-901 is described, e.g., in the published German patent application No. 2,451,769.

When all of the growth factor amino acid has been consumed, only those cells that obtained the mutation are capable of continuing their growth. The larger the population of the mutant cells induced at the starting moment of the test, the faster do they reach a spectrophotometrically measurable density. The time passing from the beginning of the test to the moment of detecting is inversely proportional to the mutagenic activity contained in the sample. The graph obtained from the growth of the populations on the basis of absorbance, the so-called growth curve, gives information, besides on the mutagenicity of the sample, also on growth factors included in it, if any.

The advantages of the method as compared with earlier tests are as follows:

1. Speed: the output of the test is obtained in less than 24 hours. With the Ames test, the output takes 48 hours, and with the fluctuation test 96 hours.
2. Lower consumption of sample and reagents, because in the turbidometric method the overall test volume is smaller.
3. Economies of material: In the turbidometric method, one sample is analyzed in one cuvette, whereas, in the Ames test, at least 6 petri dishes are required, and in the fluctuation test at least 150 test tubes per sample.
4. Economies in quantity of work: The turbidometric method can be automated completely by means of the FP-901 system. The time required per sample is about 20 seconds. In the Ames test, one sample requires at least 20 minutes, and in the fluctuation test about 1.5 hours.
5. The starting time can be selected freely during the working week: The duration of a turbidometric test is less than 24 hours, whereas the 48 hours taken by the Ames test limit the starting time to the period from Monday to Wednesday, and with the fluctuation test the starting is possible only on Monday and Thursday if no working takes place during the weekend.
6. Sensitivity: The turbidometric method is, in theory, the most sensitive possible test of bacterial mutageneity. By its means it is even possible to detect the generation of 1 induced revertant. The spontaneous revertation level of the zero control is usually lower than 1 per sample. One induced revertant cell is detected as turbid growth in about 20 hours if the G.T. (generation time) is about 40 minutes.
7. The turbidometric mutagenicity test is the only mutagenicity test in which information is also obtained between the beginning and the end of the test without interfering with the sample. In the Ames test it is possible to determine the acute toxicity of the sample, but this doubles the quantity of work required for the test. On the other hand, in the fluctuation test, attempts are made to eliminate the toxicity by means of extensive series of dilutions.

Figure 2:
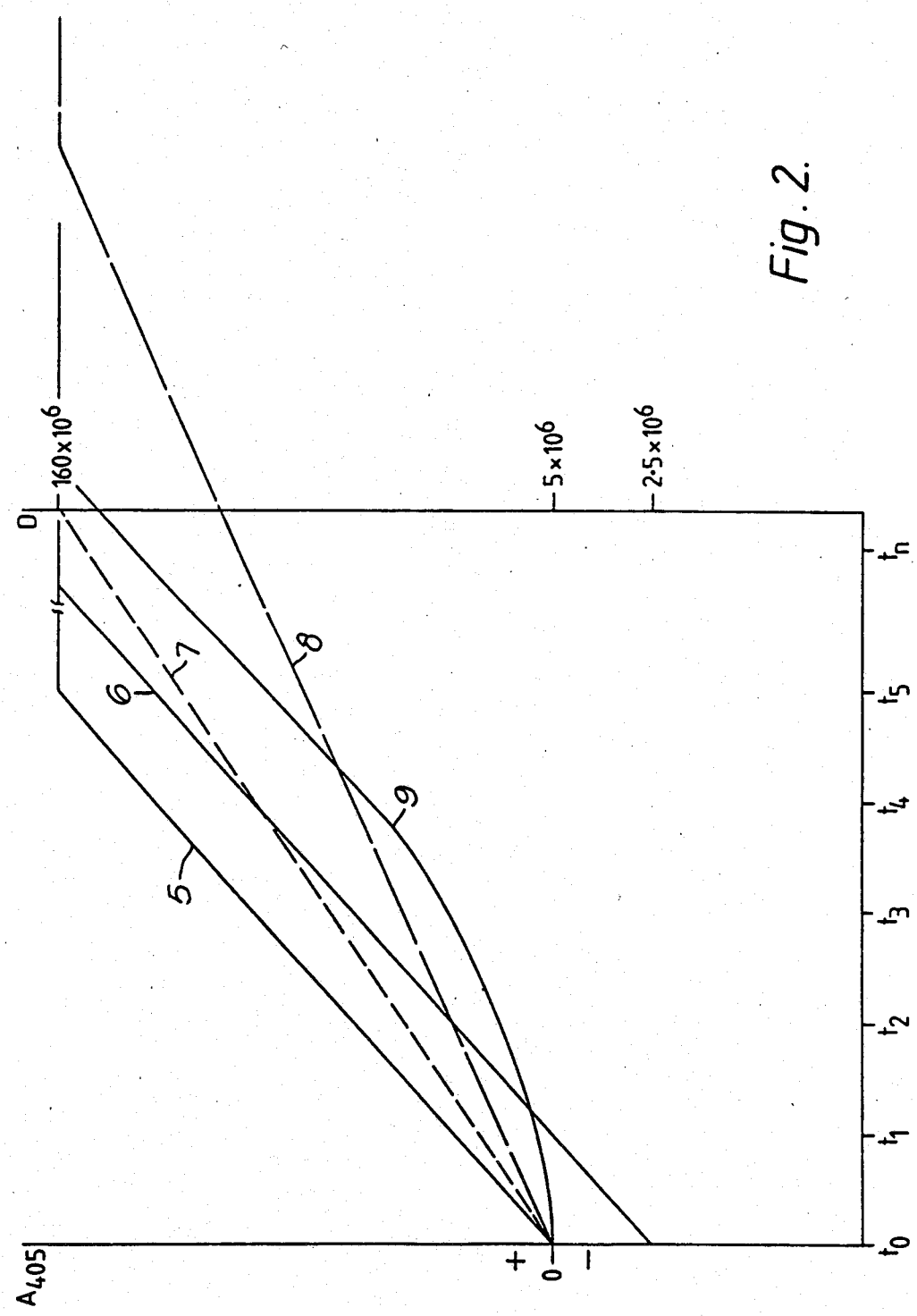

The invention and its details will be described in more detail below with reference to the attached drawings, wherein FIGS. 1 to 3 illustrate different growth curves, i.e. absorbance values, as a function of time, whereat the absorbance values are presented in the logarithmic scale.

Thus, the turbidometric test of bacterial mutagenicity is based on a differentiation, induced by a mutagen, of an originally genetically uniform cell population into auxotrophic and prototrophic sub-populations and on the observation of a change in the turbidity of these sub-populations.

The organisms used in the test are $E.coli$ WP2 (trp$^-$) and $Salmonella\ typhimurium$ (his$^-$) or any other suitable amino-acid auxotrophic single-marker strains. The growth and differentiation of the cell populations are observed by means of a FP-901 spectrophotometer that measures vertically, whereat changes in liquid volume and sedimentation of cells do not affect the result of measurement of the absorbance. $A = E\ m/a$ (Suovaniemi, O., "Performance and Properties of the Finnpipette Analyzer System", *Proceedings of the Second National Meeting on Biophysics and Biotechnology in Finland*, 1976, pp. 183–187, edited by A. -L. Kairento, E. Riihimäki and P. Tarkka; and Suovaniemi, O. and Järnefelt, J., "Discrete Multichannel Analyzing Systems with a Vertical Optical Path and Batch Processing", 1982, *International Laboratory*, in press.)

The test and the growing of cells take place in a +37° C. incubator cassette, in a 9×1 ml cuvette set, one cuvette per sample, in either Davis-Mingioli, Vogel-Bonner or any other suitable sub-minimal liquid medium. The original size of the cell population is $5 \times 10^6$, and it is used as its own blank in the FP 901, whereupon the growth of the cells causes a change in the absorbance $dA_{405}/10^6$ cells$=0.001$. At the mutagenization stage, the cells are divided auxotrophically by the effect of the growth factor 5 times. After all the growth factor has been consumed, the growth of the auxotrophic cells is at an end, but the cells that have mutated to prototrophic cells continue their growth. The higher the proportion of prototrophic cells is in the entire population, the faster do they reach a measurable density.

The time elapsed by the moment of detecting can be used directly as a measure of mutagenic activity in the case of non-toxic samples. Depending on the growth rate of the test organism, the duration of the performance of the test varies; in the case of $E.coli$ and $S.typhimurium$, it does not exceed 24 hours.

The curve obtained as an output from the absorbance values is a typical illustrator of diauxic growth.

In FIG. 1, curve 1 corresponds to uninhibited growth (non-toxicity, survival rate 100%), curve 2 corresponds to survival rate 80%, curve 3 to survival rate 50%, and curve 4 to survival rate 20%. The proportion of dead cells can be calculated from the formula $$b = n - \frac{1}{2^{t/gt}}; \text{ wherein}$$

n = proportion of original population (1.000),
t = time elapsing by the moment at which the 0-level is exceeded ($t_{0+}$, $t_1$, $t_{2+}$)
gt = generation time ($t_1 - t_0$)

In FIG. 2, curve 5 represents uninhibited growth, curve 6 a bactericide (death rate 50 %), curves 7 and 9 undecomposed bacteriostats, and curve 9 a decomposing bacteriostat.

In FIG. 3, $l_1 - l_0$ (=a) represents the share of the growth factor.

Out of the graph of diauxic growth, the following factors can be determined:

1. Toxicity of the sample, from the starting moment of the I log stage (FIG. 1).
2. Nature of the toxicity of the sample (bactericide, bacteriostat, decomposing bacteriostat), from the form of the growth curve of stage I log (FIG. 2).
3. Growth rate of non-reverted cells, from the magnitude of the angle factor of the growth curve of the stage I log (FIG. 3).
4. Growth rate of the revertants, from the magnitude of the angle factor of the stage II log (FIG. 3).
5. Growth factors, if any, present in the sample, from the magnitude of the absorbance in the I plateau stage. The number of extra revertants caused by the growth factors is found out from the formula $Fp. = 2^{g-1} \times g \times r$, wherein Fp. = extra revertants after consumption of extra growth factor, g = number of cell generations, r = quantity of revertants produced per generation × population size; z = revertants (r) per generation (g) x population size (s) $l_0$ = starting level of excess = $D_1-D_0$ = s $l_1$ = final level of excess = $D_2-D_0$ g = number of cell generations = $D_1 - D_0 D_2 = k_1/t_{5+} - t_0 - k_1/t_5 - t$
6. Mutageneity of the sample, from the length of the I plateau stage (FIG. 3).
7. Number of revertants at the moment $t_0$, by extrapolation by taking advantage of the growth rates of the stages II log and I log. D = detected size of final population $a = k_1/t_5 - t_0$ = number of divisions in stage log I $b = K_2/t_{N+2} - t_5$ = number of divisions in the stages plateau I and log II X = number of revertants at the time $t_0$.

$$X = \frac{D}{\cdot 2^a + 2^{a+b}}$$

Performance of the test

| | |
|---|---|
| Growth medium | 965 μl |
| Bacteria cells | 5 μl |
| Sample | 10 μl |

Metabolic activation system (S-9) 20 μl (if required)

The above components are combined in a 1 μl cuvette, stirred by means of a shaker for 15 seconds, placed in a +37° C. incubator cassette, blanked at a wave length of 405 nm in a FP 901, thereupon incubated for 20 to 24 hours, during which time the absorbance of the sample is measured at 405 nm in accordance with a preprogrammed time share system.

From the absorbance values, a growth curve is formed as a function of time, from which the mutageneity of the sample and several other parameters can be interpreted.

The turbidometric test of bacterial mutageneity is suitable for all types of mutageneity testing in which it is to be found out whether the sample concerned is capable of reacting with DNA in a way causing mutations.

TABLE 1

Turbidity distinction power of FP-901 $A_{405\ nm}$ n = 9

| Density $10^6$ | $A_{405}\pm$ | S.D. | S.D./$A_{405}$ (%) | $A_{405}/10^6$ cells |
|---|---|---|---|---|
| 5 | 0.000 | 0.000 | — | — |
| 20 | 0.021 | 0.004 | 19 | 0.001 |
| 40 | 0.046 | 0.007 | 15 | 0.001 |
| 60 | 0.062 | 0.006 | 10 | 0.001 |
| 80 | 0.076 | 0.002 | 2.6 | 0.001 |
| 160 | 0.159 | 0.010 | 6.0 | 0.001 |
| 240 | 0.239 | 0.010 | 4.2 | 0.001 |
| 320 | 0.326 | 0.015 | 4.6 | 0.001 |
| 400 | 0.405 | 0.018 | 4.4 | 0.001 |
| 480 | 0.486 | 0.020 | 4.1 | 0.001 |
| 560 | 0.562 | 0.022 | 3.9 | 0.001 |
| 640 | 0.638 | 0.015 | 2.4 | 0.001 |
| 720 | 0.706 | 0.015 | 2.1 | 0.001 |
| 800 | 0.772 | 0.014 | 1.8 | 0.001 |
| 880 | 0.833 | 0.012 | 1.4 | 0.001 |
| 960 | 0.890 | 0.009 | 1.0 | 0.001 |
| 1040 | 0.938 | 0.011 | 1.2 | 0.001 |
| 1120 | 0.990 | 0.010 | 1.0 | 0.001 |

TABLE 2

Effect of growth factors on density and auxotrophic growth time of E. coli WP 2 uvrA. Size of initial population $5 \times 10^6$ cells.

| Trp-conc. μg/ml | Density/measurem. cuvette | Growth time |
|---|---|---|
| 0.0 | $2.5 \times 10^7$ | 2 h 20' |
| 0.4 | $1.6 \times 10^8$ | 5 h |
| 0.8 | $2.0 \times 10^8$ | 5 h 20' |
| 1.6 | $3.2 \times 10^8$ | 6 h |
| 3.2 | $6.4 \times 10^8$ | 7 h |
| 6.4–48 | n. $10^9$ | 8 h 20' |

What is claimed is:

1. A method for performing a mutagenicity test comprising the steps of;
    (a) subjecting a uniform auxotrophic cell population to a mutagen to be tested, in a medium containing a growth factor;
    (b) allowing the cell population to undergo differentiation so that cell population is composed of cell subpopulations;
    (c) growing the differentiated subpopulations in a medium free from the growth factor; and
    (d) measuring variation in turbidity of the mediums containing the subpopulations as a change in optical density, said variations measured vertically at a fixed wavelength.
2. The method according to claim 1 wherein the variation in turbidity is measured by a photometer.
3. The method according to claim 1 or 2, wherein the optical density values are measured in accordance with a pre-programmed time share system and a growth curve is formed from the values as a function of time.

* * * * *